United States Patent [19]

Dodson et al.

[11] 4,086,265
[45] Apr. 25, 1978

[54] PREPARATION OF CATECHOL DERIVATIVES

[75] Inventors: Raymond M. Dodson, Fridley, Minn.; Joseph B. Hanson, Wheaton, Ill.

[73] Assignee: The Regents of the University of Minnesota, Minneapolis, Minn.

[21] Appl. No.: 746,254

[22] Filed: Dec. 1, 1976

[51] Int. Cl.² .................. C07C 153/09; C07C 149/30; C07C 67/08
[52] U.S. Cl. ......................... 260/455 A; 260/609 D; 260/327 M; 560/130; 260/516; 260/340.5 R
[58] Field of Search .......... 260/455 A, 609 D, 479 R

[56] References Cited

U.S. PATENT DOCUMENTS

| | | | |
|---|---|---|---|
| 1,968,905 | 8/1934 | Palmer | 260/609 D |
| 1,968,906 | 8/1934 | Palmer | 260/609 D |
| 2,004,728 | 6/1935 | Palmer | 260/609 D |

OTHER PUBLICATIONS

H. R. Al-Kazimi et al., *J. Amer. Chem. Soc.*, 77, 2479, (1955).
H. Kwart et al., *J. Org. Chem.*, 31, 410, (1966).
M. S. Newman et al., *J. Org. Chem.*, 31, 3980, (1966).

*Primary Examiner*—Lewis Gotts
*Assistant Examiner*—Robert C. Whittenbaugh
*Attorney, Agent, or Firm*—Burd, Braddock & Bartz

[57] ABSTRACT

A method of preparing derivatives of aromatic compounds including the catechol function

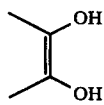

by replacement of one of the hydroxyls by mercaptan

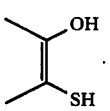

Cathechol or a multi-ring compound (naphthyl-, anthryl-, phenanthryl-, etc.) containing the catechol function is first reacted with thiophosgene to produce the corresponding dioxole-2-thione

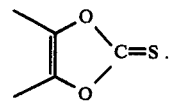

The thione is ammonolyzed to the corresponding hydroxy N,N-disubstituted thionocarbamate

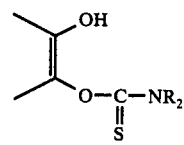

The thionocarbamate is acetylated to

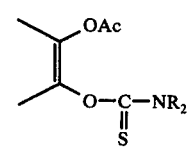

and heated to rearrange the compound to the corresponding thiolcarbamate

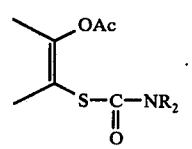

Further heating produces the corresponding oxathiol-2-one

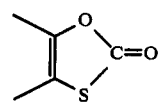

which can be hydrolyzed to the corresponding mercaptan

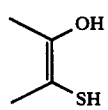

15 Claims, 2 Drawing Figures

PREPARATION OF CATECHOL DERIVATIVES

BACKGROUND OF THE INVENTION

1. Field of the Invention

The invention relates to the synthesis of mercaptans derived from corresponding catechols via the thionocarbamate-thiolcarbamate rearrangement by replacement of one of the hydroxyls by mercaptan. The invention encompasses catechol (1,2-dihydroxybenzene) and multi-ring aromatic compounds containing the catechol function, i.e., two adjacent hydroxyls on any ring.

2. The Prior Art

The chemical preference of divalent sulfur for forming single rather than double bonds to carbon is well known. It is not surprising, therefore, that the reactivity of thiocarbonyls is quite different from that of their oxygen analogues. The thermal transformation of aryl thionocarbonates into the corresponding thiolcarbonates has been called the Schönberg rearrangement after Alexander Schönberg, who first observed it in 1929. [A. Schönberg and L. Varga, Chem. Ber. 63, 178 (1930); A. Shönberg, L. Varga, and W. Paul, Ann. Chem., 483, 107, (1930)]:

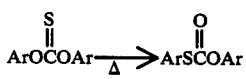

Schönberg summarized his observations by 3 empirical rules for the rearrangement:

(1) The rearrangement will proceed only in acyclic systems. Cyclic thionocarbonates, such as

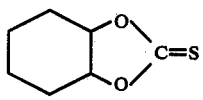

will not rearrange.

(2) In all cases observed, the rearrangement proceeded from a higher melting to a lower melting compound.

(3) The carbon atom on which a bond to oxygen is broken in the rearrangement is the same carbon atom to which a bond to sulfur is formed. That is to say, there is no secondary rearrangement. The substitution pattern on the aryl portion of the molecule is not altered.

Schönberg pointed out the significance of the thionocarbonate rearrangement as providing a means of converting phenols into their thio analogues. He did not, however, actually reduce his disulfides to thiophenols.

Tarbell and coworkers [H. R. Al-Kazimi, D. S. Tarbell, and D. Plant, J. Amer. Chem. Soc., 77, 2479 (1955)] pursued the investigation of the thionocarbonate rearrangement, but not until 25 years after Schönberg's work. Their study involved the thermal rearrangement of 12 thionocarbonates, of which 6 were unsymmetrical (X ≠ Y):

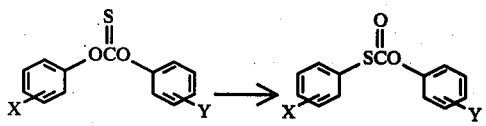

Tarbell hydrolyzed his thiolcarbonates and then oxidized the resulting substituted thiophenols to disulfides, thus extending the scope of the general synthetic method suggested by Schönberg.

Kwart and Evans [H. Kwart and E. R. Evans, J. Org. Chem., 31, 410 (1966)] suggested that the thionocarbonate rearrangement ought to proceed in the vapor phase. The advantage of a vapor phase reaction is that by avoiding prolonged heating in a polar medium one might also avoid side reactions and decompositions which consume both products and reactants. Kwart and Evans investigated the rearrangement of bis-(0-2-allylphenyl) thionocarbonate:

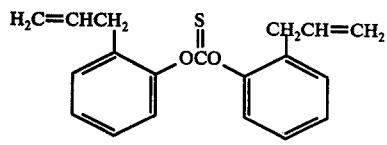

The results supported their original contentions about the thionocarbonate rearrangement. More important was their application of the method and principle to thionocarbamates. They were able to predict and demonstrate a thermal rearrangement of thionocarbamates to thiolcarbamates, in analogy to the thionocarbonate rearrangement.

The superiority of the thionocarbamate rearrangement to the Schönberg method for synthesis of thiophenols was immediately recognized and pursued by Newman and Karnes [M. S. Newman and H. A. Karnes, J. Org. Chem., 31, 3980 (1966)]. Even at maximum efficiency, rearrangement of a thionocarbonate can only provide 1 mole of thiophenol for every 2 moles of phenol in the starting material. On the other hand, the conversion of phenols to thiophenols via a thionocarbamate rearrangement is theoretically 100 percent efficient.

Newman and Karnes prepared over 30 substituted O-aryl dialkyl-thionocarbamates by base catalyzed addition of substituted phenols to N,N-dialkylthiocarbamyl chlorides:

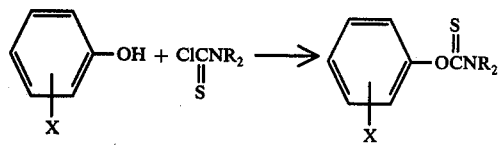

In most cases, thermal rearrangement of these products to the corresponding thiolcarbamates required lower temperatures and shorter reaction times, and gave better yields than the corresponding thionocarbonate rearrangements by Tarbell. Newman's thiolcarbamates were hydrolyzed in good yield to substituted thiophenols. There were significant exceptions to the usually successful rearrangements of thionocarbamates by Newman, however. More significant is Newman's report that 4 compounds, 3 of them derivatives of catechol, failed to rearrange even at high temperature, but decomposed to tar:

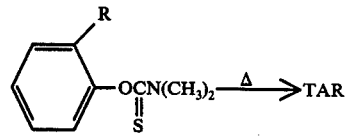

-continued where R = 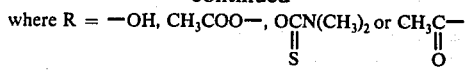

The apparent exclusion of catechols from conversion by this method to mono-thio catechols excludes a very large family of natural products bearing the catechol function, as well as many synthetically useful catechol derivatives, 2-methoxyphenyl thionocarbamate, a catechol der vative, rearranged, but only at very high temperature (290° C). The scope of Newman and Karnes' investigation firmly establishes the thionocarbamate-thiolcarbamate rearrangement as the method of choice for conversion of phenols to thiophenols. Applicants pursued this route to synthesize thio derivatives of catechols in spite of the previous failures.

(A more comprehensive review of the prior art can be found in "Extrusions and Sulfur-Oxygen Rearrangements of Catechol Derivatives" (1976), the doctoral thesis of Joseph B. Hanson, one of the applicants herein, available from Xerox University Microfilms, Ann Arbor, Mich., and incorporated herein by reference.)

SUMMARY OF THE INVENTION

Broadly stated, the invention comprises the method of preparing catechol derivatives containing the function:

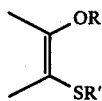

in which R is either hydrogen or an acetyl group and R' is either hydrogen or a carbamate group

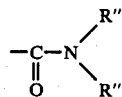

in which R" may be either hydrogen or a lower alkyl group. Some such compounds are useful as herbicides having weed killing properties. Others have demonstrated biological activity. The method is carried out by reacting catechol or a multiple ring aromatic compound containing the catechol function, i.e., two adjacent hydroxyls on an aromatic ring, with thiophosgene to produce the corresponding dioxole-2-thione

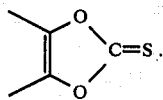

This thione is ammonolyzed with ammonia or an amine to the corresponding hydroxy N,N-substituted thionocarbamate

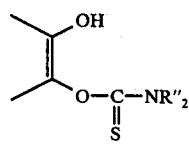

in which R" may be either hydrogen or lower alkyl and either the same or different. The thionocarbamate is acetylated to the corresponding acetoxy N,N-disubstituted thionocarbamate, which upon heating rearranges to the corresponding thiolcarbamate

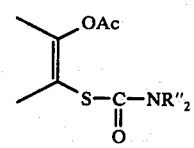

Certain of these intermediate compounds are useful, or they may be heated further to produce the corresponding oxathiole-2-one

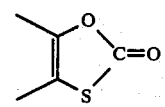

which, upon hydrolysis produces the corresponding mercaptophenol

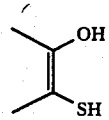

BRIEF DESCRIPTION OF THE DRAWINGS

FIG. 1 is a schematic illustration of the invention showing the conversion of catechol to 2-mercaptophenol.

DETAILED DESCRIPTION OF THE PREFERRED EMBODIMENTS

Figure 2:
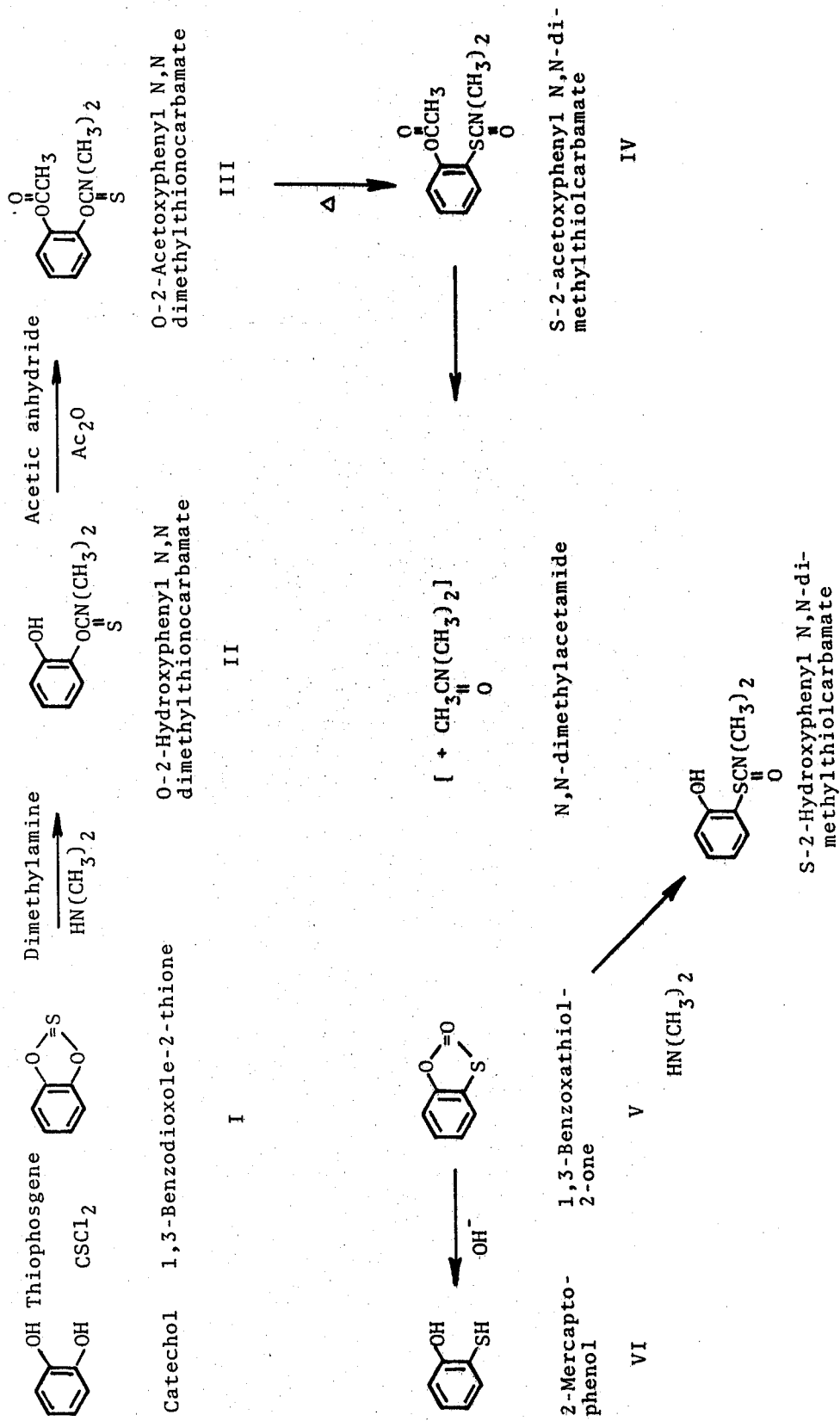
FIG. 2 is a similar illustration of the synthesis of a biologically active catechol derivative prepared according to the invention.
Figure 2:
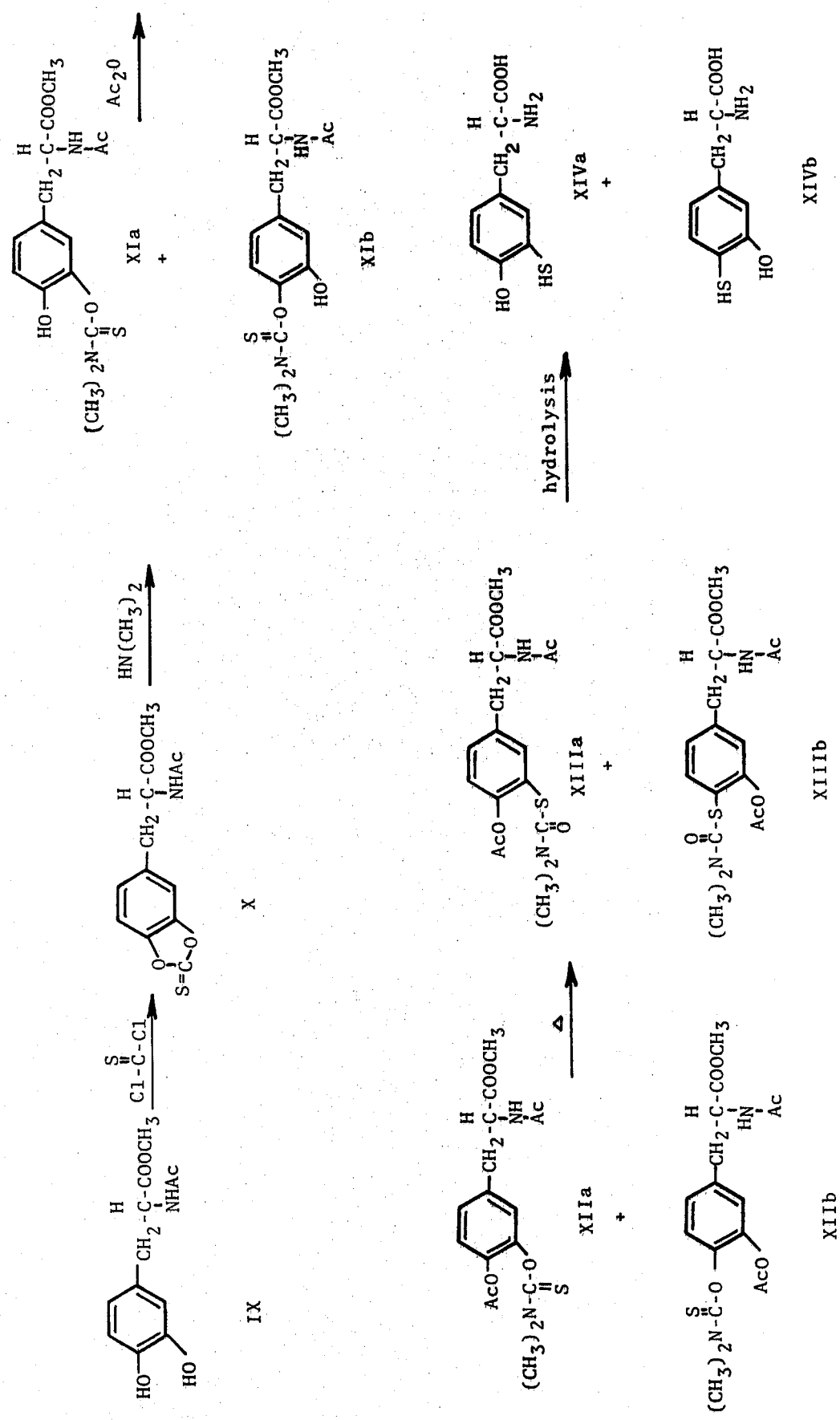

The starting material may be catechol or a multiple aromatic ring compound containing the catechol function, all of which are defined herein as catechols and derivatives of which are defined as catechol derivatives. Included are compounds such as 2,3-naphthalenediol, 1,2-anthracenediol, 9,10-phenanthrenediol, and the like. The aromatic rings may include up to two further substituent groups.

The catechol starting material is converted to a cyclic aryl thionocarbonate by base catalyzed reaction with thiophosgene (ClCSCl). The thiophosgene is added slowly slightly in excess of molar proportion to a solution of the catechol in aqueous solution of sodium hydroxide at low temepratures (5° to 10° C) for good yields.

The resulting thione is ammonolyzed by treatment with ammonia or a primary or secondary amine in a solvent, such as benzene, at room temperature with stirring for several hours. The attached amine radicals are lower alkyl groups and may be the same or different. Useful amines include dimethylamine, diethylamine, methylethylamine, N-propylamine, N-butylamine, and the like.

The resulting hydroxyaryl thionocarbamate is acetylated by treatment with acetic anhydride or acetyl chloride in a solvent at room temperature for several hours to selectively protect the hydroxyl group not of interest for derivatization.

The corresponding acetoxyaryl thionocarbamate is rearranged by thermolysis to the corresponding thiolcarbamate. Heating is carried out in the absence of air at about 200° to 260° C for about 20 minutes to 3 hours. Quantitative rearrangement occurs to a mixture of the corresponding acetoxyaryl disubstituted thiolcarbamate, aryloxathiole-2-one and an amide.

The aryloxathiolone is separated by distillation and is easily converted to the corresponding mercaptophenol by base catalyzed hydrolysis in the absence of air. The corresponding rearranged hydroxyarylthiolcarbamate is prepared by treatment of the aryloxathiolone with ammonia or an amine in a solvent.

The intermediate catechol derivatives of the type:

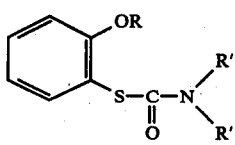

in which R is hydrogen or an acetyl group and R' is hydrogen, methyl or ethyl show promise as herbicides, specifically as weed killers. The same intermediates with a

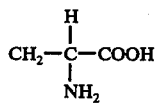

in the 4 position are useful in the production of mercaptophenols of known biological activity. The invention is further illustrated by the following examples.

EXAMPLE I

Conversion of Catechol to 2-Mercaptophenol

The step-by-step conversion of catechol to 2-mercaptophenol (VI) according to the method of this invention is illustrated in the drawing and was carried out as follows:

1,3-Benzodioxole-2-thione (I)

To 200 ml of aqueous sodium hydroxide (16.00 g, 0.400 mol) at 5° was added catechol (22.00 g, 0.200 mole). The resulting dark green solution was stirred magnetically and maintained at 5°-10° while thiophosgene (17 ml, 25.5 g, 0.22 mol) was added dropwise over 2 hours. The green color of the solution was discharged during the addition and an orange-brown precipitate formed. The mixture was filtered through a Büchner funnel into a saturated solution of aqueous sodium hydroxide to destroy any residual thiophosgene. The solid thus collected on the funnel was washed with 1.5 l of water and dried to give 27.41 (90 percent) of the crude 1,3-benzodioxole-2-thione (I): mp 151°-153° (sealed capillary; lit. mp 154°, 158°-158.5°). Sublimation twice at 150° (1 atm) gave white needles in 81 percent overall yield (lit. 25 percent): mp 158°-159.5° sealed capillary).

O-2-Hydroxyphenyl N,N-dimethylthionocarbamate (II)

1,3-Benzodioxole-2-thione (I) (71.0 g, 0.467 mol) was dissolved in 1.5 l of benzene. Dimethylamine (21.1 g, 0.468 mol) was added in one portion, and the solution was stirred at room temperature under nitrogen for 9 hours. The solvent was then removed on the rotary evaporator to give 94.8 (103 percent) of viscous yellow oil. Chromatography of 12.0 g of the oil on a column of silica gel (200 g), elution with 3:7 ether:methylene chloride, and crystallization from ether/petroleum ether (bp 60°-70°) of the solid thus obtained gave 9.1 g (79 percent) of white prisms, mp 65.5°-68°. A second crystallization gave the analytical sample, mp 65.5°-67.5°.

O-2-Acetoxyphenyl N,N-dimethylthionocarbamate (III)

O-2-Hydroxyphenyl N,N-dimethylthionocarbamate (II) (10.00 g, 0.051 mol) and pyridine (5.92 g, 0.075 mol) were dissolved in 200 ml of anhydrous ether. Acetic anhydride (7.65 g, 0.075 mol) was added in one portion and the solution was stirred at room temperature for 24 hours. A crystalline white solid precipitated from the solution as the reaction proceeded. Concentration of the reaction mixture on the rotary evaporator to a total volume of 75 ml caused formation of more solid. The mixture was filtered and the solid was washed on the funnel with 35 ml of cold ether to give 9.15 g of the acetate: mp 102°-104° (lit. mp 102°-104°). The filtrate, concentrated to 50 ml, was washed with 5 × 50 ml portions of water and dried over anhydrous sodium sulfate. The solvent was removed on the rotary evaporator to give an additional 1.49 g of solid, mp 100°-103°. The overall yield of O-2-acetoxyphenyl N,N-dimethylthionocarbamate (III)) was 87 percent.

Thermal Rearrangement of O-2-Acetoxyphenyl N,N-dimethylthiocarbamate (III)

O-2-Acetoxyphenyl N,N-dimethylthionocarbamate (III) (15.00 g, 0.063 mol) was heated without solvent at 250° under a slow current of dry nitrogen. The solid melted and refluxed gently. After 3 hours ir and NMR spectra of the reaction mixture indicated quantitative rearrangement to a mixture of S-2-acetoxyphenyl N,N-dimethylthiolcarbamate (IV), 1,3-benzoxathiole-2-one (V), and N,N-dimethylacetamide in a 1.0:7.6:7.6 molar ratio, respectively. Less than 1 percent of the starting material remained. Similar experiments run at lower temperatures and/or for shorter lengths of time gave higher proportions of starting material and S-2-acetoxyphenyl N,N-dimethylthiolcarbamate (IV) (e.g., reaction at 180° for 3 hours gave a 1.0:3.0:1.7:1.7 molar ratio of starting material, IV, V and N,N-dimethylacetamide, respectively). No reaction was observed at 155°. Spectra of mixtures were interpreted by comparison to spectra of authentic samples of the individual components. Depending on the composition of the reaction mixture and the product desired, the reaction mixture could be treated by one of the procedures given below.

A. Base catalyzed hydrolysis of 1,3-Benzoxathiole-2-one (V) to 2-Mercaptophenol (VI)

The crude reaction mixture obtained by heating O-2-acetoxyphenyl N,N-dimethylthionocarbamate (III) (1.00 g, 0.004 mol) at 260° for 20 minutes under a current of nitrogen was shown by NMR to contain a 1:3:4:4 molar ratio of starting material, S-2-acetoxyphenyl N,N-dimethylthiolcarbamate (IV), 1,3-benzoxathiol-2-one (V), and N,N-dimethylacetamide, respectively. The mixture was refluxed with 25 ml of aqueous 10 percent sodium hydroxide for 1 hour. After 20 minutes, the mixture became homogeneous and turned brown.

Acidification by dropwise addition of HCl caused the solution to turn milky and full of oily droplets. Extraction with 3 × 30 ml portions of ether, combination and drying of the ether extracts over anhydrous $MgSO_4$, and removal of solvent on the rotary evaporator gave 0.25 g (55 percent) of 2-mercaptophenol (VI) as a pale yellow liquid. Other experiments produced 2-mercaptophenol in yields up to 88 percent. 2-Mercaptophenol is a useful intermediate in the production of pesticides, insecticides and bactericides.

B. Formation of 1,3-Benzoxathiol-2-one (V) by Treatment of IX with aqueous acid The composition of a crude reaction mixture (0.45 g) from the thermal rearrangement of O-2-acetoxyphenyl N,N-dimethylthionocarbamate (III) was shown by NMR to be a 3.2:1 molar mixture of S-2-acetoxyphenyl N,N-dimethylthiolcarbamate (IV) and starting material. The mixture was refluxed with 20 ml of aqueous 10 percent HCl for 3 hours and extracted with 30 ml of chloroform. The chloroform extract was dried over anhydrous sodium sulfate and the solvent was stripped on the rotary evaporator to give 0.20 g of pale yellow liquid. An NMR spectrum indicated this to be a 1:6.2 molar mixture of catechol and 1,3-benzoxathiol-2-one (V). Overall yield of 1,3-benzoxathiol-2-one (V) based on the amount of O-2-acetoxyphenyl N,N-dimethylthiolcarbamate (III) in the original mixture was 82 percent.

This procedure was applied to the crude rearrangement product obtained from thermolysis (250°/3 hrs.) of 15.00 g of III. 1,3-Benzoxathiol-2-one (V) was isolated in 77 percent yield (7.33 g) based on the initial starting material III.

C. Separation of 1,3-Benzoxathiol-2-one (V) by Chromatography on silica

Thermal rearrangement of O-2-acetoxyphenyl N,N-dimethylthionocarbamate (III) (2.00 g, 0.008 mol; 250°/3hrs./900 psi $N_2$ in a stainless steel bomb) gave a crude reaction mixture consisting of 1,3-benzoxathiol-2-one (V) and N,N-dimethylacetamide, with only a trace of S-2-acetoxyphenyl N,N-dimethylthiolcarbamate (IV). The mixture was chromatographed on 85 g of silica gel eluted with chloroform-ether (35:65) to give 0.95 g of brown liquid. An NMR spectrum indicated a mixture of 1,3-benzoxathiol-2-one (V), catechol, and S-2-acetoxyphenyl N,N-dimethylthiolcarbamate (IV) in a 1:0.09:0.06 molar ratio, respectively. Overall yield of 1,3-benzoxathiol-2-one (V) was 64 percent. A small amount (0.06 g) of N,N-dimethylacetamide was also isolated in later fractions, and identified by comparison of NMR and ir spectra to those of an authentic sample.

D. Separation of 1,3-Benzoxathiol-2-one (V) by Vacuum Distillation

An NMR spectrum of the crude reaction mixture of a thermal rearrangement of O-2-acetoxyphenyl N,N-dimethylthionocarbamate (II) (8.50 g, 0.035 mol; 250°/2.5 hrs./$N_2$) indicated a molar ratio of 8.5:8.3:1 of 1,3-benzoxathiol-2-one (V), N,N-dimethylacetamide, and S-2-acetoxyphenyl N,N-dimethylthiolcarbamate (IV), respectively. Vacuum distillation of the mixture gave 4.05 g (75 percent) of 1,3-benzoxathiol-2-one (V), bp 69°-72° (0.25 mm), as an almost colorless liquid. Redistillation of this material gave a single fraction, bp 62°-64° (0.15 mm; lit. bp 93°-96°/2.5 mm): mp 25.8°-27° (lit. mp 26°).

S-2-Hydroxyphenyl N,N-dimethylthiolcarbamate (VII)

1,3-Benzoxathiole-2-one (V) (6.30 g, 0.041 mol) and dimethylamine (2.2 g, 0.045 mol) were dissolved in 150 ml of benzene. An NMR spectrum of a 1 ml aliquot which was removed and completely stripped of solvent on the rotary evaporator after less than 5 minutes showed the reaction to be 93 percent complete. After 2 hours the reaction mixture was stripped of solvent on the rotary evaporator to give 8.3 g (101 percent) of pale yellow solid. This material was digested with 25 ml of ether, which was then decanted. The remaining white solid was recrystallized from chloroform-ether to give fine white prisms of S-2-hydroxyphenyl N,N-dimethylthiolcarbamate (VII) (5.83 g, 66 percent), mp 98.5°-100°. An analytical sample was recrystallized again, mp 98°-100°.

EXAMPLE II

An alternative method of preparation of 2-mercaptophenol (VI) is as follows: 1,3-Benzoxathiol-2-one (V) (2.80 g, 0.018 mol) was refluxed under nitrogen with 25 ml of 10 percent aqueous sodium hydroxide for 20 minutes. The initially colorless 2-phase mixture became a homogeneous pale brown solution. The solution was acidified by dropwise addition of HCl and then extracted with 2 × 25 ml of chloroform. The combined portions of chloroform were washed with three 50 ml portions of water, dried over anhydrous $MgSO_4$, and stripped of solvent on the rotary evaporator to yield 2.04 g (88 percent) of crude, pale yellow 2-mercaptophenol (VI). Vacuum distillation gave a colorless, foul-smelling liquid, bp 35°-37° (0.15 mm): 1.48 g (64 percent).

EXAMPLE III

The preparation of 1,3-benzoxathiol-2-one (V) by thermal reaction of S-2-acetoxyphenyl N,N-dimethylthiolcarbamate (IV) is as follows: S-2-Acetoxyphenyl N,N-dimethylthiolcarbamate (IV) (0.25 g, 0.001 mol) was put into a small pear-shaped flask fitted with a condenser. The entire system was flushed well with dry nitrogen and then maintained under a slow nitrogen current as the flask and its contents were immersed for 15 minutes in a Wood's alloy bath which had been preheated to 250°. A colorless liquid distilled on the walls of the condenser. The liquid in the condenser was identified as N,N-dimethylacetamide from its ir spectrum which was identical with that of an authentic sample. An NMR spectrum of the reaction mixture in the pot showed a molar ratio of 3.2:1 of 1,3-benzoxathiol-2-one (V) to dimethylacetamide.

EXAMPLE IV

Preparation of Naphtho[2,3-α]-1-3,oxathiol-2-one

Another demonstration of the conversion of a catechol function to its mono-thio analogue was achieved with 2,3-naphthalenediol.

Naphtho[2,3-α]-1,3-dioxole-2-thione 2,3-Naphthalenediol (16.0 g, 0.100 mol) was added to 125 ml of aqueous sodium hydroxide (8.0 g, 0.200 mol). The solution was stirred magnetically and cooled to 10°. Thiophosgene (10 ml, 15 g, 0.13 mol) was added dropwise over 20 minutes such that the reaction temperature did not exceed 12°. A thick brown precipitate formed in the mixture. When the thiophosgene addition was complete, the mixture was stirred for 1 hour at 10°. The precipitate was then separated from the mixture by filtration and washed well with water on the filter to give 18.0 g (89 percent) of the crude, pale brown naphtho[2,3-a]-1,3-dioxole-2-thione, mp (sealed capillary) 246°-249° (dec) after drying.

O-(3-Hydroxy-2-naphthyl) N,N-dimethylthionocarbamate

Naphtho[2,3-a]-1,3-dioxole-2-thione (10.11 g, 0.050 mol) was partially dissolved in 150 ml of benzene. Dimethylamine (2.84 g, 0.631 mol) was added, and the mixture was stirred at room temperature for 18 hours, during which time it became homogeneous. The solvent was stripped to give 13.0 g (105 percent) of pale brown solid. Reaction with dimethylamine gave O-(3-hydroxy-2-naphthyl) N,N-dimethylthionocarbamate.

O-(3-Acetoxy-2-naphthyl) N,N-dimethylthionocarbamate

The product was acetylated with acetic anhydride and pyridine to O-(3-acetoxy-2-naphthyl) N,N-dimethylthionocarbamate.

Naphtho[2,3-a]-1,3-oxathiol-2-one

O-(3-Acetoxy-2-naphthyl) N,N-dimethylthionocarbamate (10.60 g, 0.037 mol) was placed in a 50 ml three-necked flask which was then flushed with argon for 15 minutes. The flask and its contents, still under a gentle current of argon, were immersed for 15 minutes in a Wood's alloy bath which had been preheated to 250°. The product was 10.5 g of viscous black oil. An infrared spectrum of the oil displayed three carbonyl absorptions corresponding to the carbonyl absorption frequencies of N,N-dimethylacetamide, naphtho[2,3-d]-1,3-oxathiol-2-one and naphtho[2,3-d]-1,3-dioxol-2one, respectively. The oil was taken up in 100 ml of chloroform, washed with two 200 ml portions of aqueous 10 percent HCl and five 150 ml portions of water. The solution was dried over anhydrous sodium sulfate and stripped of solvent on the rotary evaporator to give 6.56 g of brown oil. A portion of the oil (1.00 g) was heated to 150° under vacuum (0.15 mm Hg) causing 0.81 g of a waxy yellow solid to sublime. Trituration of the solid with 25 ml of ether, in small portions, gave 0.34 g of white solid that was crystallized from ether-methylene chloride to give 0.21 g of white powder (mp 124°-127°). An infrared spectrum of the powder was identical to one of a sample of naphtho[2,3-d]-1,3-oxathiol-2-one whose identity was confirmed by a high resolution mass spectrum. Overall yield: 18 percent. The product upon base catalyzed hydrolysis can be converted to the corresponding mercaptophenol.

EXAMPLE V

W. B. Lutz, C. R. Creveling, J. W. Daly and B. Witkop (J. Med. Chem., 15, 795 (1972)) have shown that the compound:

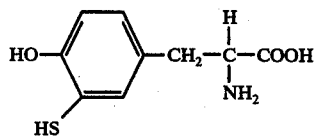

has useful biological activity. This compound can be made by the method of this invention by the following sequence of reactions, as illustrated in FIG. 2 of the drawings. The substituted catechol (IX) is converted by base catalyzed addition of thiophosgene to the corresponding dioxole-2-thione (X). Reaction with dimethylamine gives the corresponding O-2-hydroxy-substituted phenyl N,N-dimethylthionocarbamate isomers (XIa and XIb). Acetylation with acetic anhydride and pyridine gives the corresponding O-2-acetoxy-substituted phenyl N,N-dimethylthionocarbamate isomers (XIIa and XIIb). Thermolysis under nitrogen at 250° gives the rearranged S-2-acetoxy-substituted phenyl N,N-dimethylthiolcarbamate isomers (XIIIa and XIIIb) which upon base catalyzed hydrolysis produces the corresponding substituted mercaptophenol isomers (XIVa and XIVb) from which the biologically active compound (XIVa) can be separated.

EXAMPLE VI

Phenanthro[9-10-a]-1,3-dioxole-2-thione was prepared as follows as a starting material for production of the monothio analogue of 9,10-phenanthrenediol according to the present invention. Sodium hydroxide (0.80 g, 0.020 mol) was dissolved in 150 ml of water which had been freshly boiled and cooled under a stream of nitrogen. The solution was cooled to 5°, stirred magnetically and maintained under a slow current of nitrogen. 9,10-Phenanthrenediol (2.10 g, 0.01 mol) was added in one portion. To the resulting dark green solution was added thiophosgene (4.65 g, 0.040 mol) dropwise over 10 minutes. The green color was discharged and a yellow-orange precipitate formed. When the addition was complete, the mixture was stirred 30 minutes longer at 5° and then was allowed to come to room temperature. Excess thiophosgene was aspirated from the mixture into a solution of aqueous sodium hydroxide. The mixture was then filtered and the solid obtained was washed on the filter with 200 ml of water and dried to give 2.35 g (81 percent) of pink solid, mp 190°-193°. A portion of the material was crystallized twice from ethyl acetate-petroleum ether (bp 60°-70°) to give an analytical sample fo pink-orange crystals, mp 196°-198°. The product may then be ammonolyzed to the corresponding hydroxyphenanthryl thionocarbamate, acetylated to the corresponding acetoxyphenanthryl thionocarbamate, rearranged by heating to the corresponding thiolcarbamate and to the phenanthro[9,10-a]-1,3-oxathiole-2-one. Finally, this latter compound may be hydrolyzed to the corresponding mercaptophenol.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of preparing catechol derivatives containing the function:

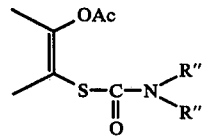

wherein R" is selected from the class consisting of hydrogen and lower alkyl groups, which method comprises:

(A) reacting an aromatic compound containing the catechol function

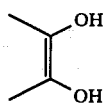

with thiophosgene to produce a thione having the function

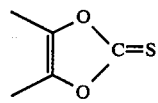

(B) ammonolyzing said thione by reacting with an agent selected from the class consisting of ammonia and lower alkyl amines to form a hydroxyaryl thionocarbamate having the function

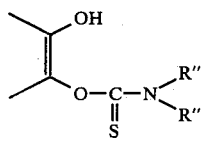

wherein R" is selected from the class consisting of hydrogen and lower alkyl groups,
(C) acetylating said thionocarbamate to form the corresponding acetoxyaryl thionocarbamate, and
(D) heating in the absence of air to about 200° to 260° C for about 20 minutes to 3 hours to rearrange said thionocarbamate to form the corresponding acetoxyaryl thiolcarbamate having the function

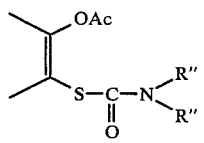

2. A method according to claim 1 further characterized in that said aromatic compound containing the catechol function is selected from the class consisting of catechol, 2,3-naphthalenediol, 9,10-phenanthrenediol and corresponding substituted diols.

3. A method according to claim 1 further characterized in that said ammonolyzing agent is selected from the class consisting of ammonia, dimethylamine, diethylamine, methylethylamine, N-propylamine and N-butylamine.

4. A method according to claim 1 further characterized in that said hydroxyaryl thionocarbamate is acetylated by reaction with an acetylating agent selected from the class consisting of acetic anhydride and acethylchloride.

5. A method according to claim 1 further characterized in that thiophosgene is reacted with said compound containing the catechol function in basic solution slowly over from about 40 minutes to 2 hours at a low temperature between about 5° to 10° C.

6. A method of preparing catechol derivatives containing the function:

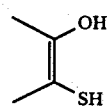

which method comprises:
(A) reacting an aromatic compound containing the catechol function

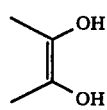

with thiophosgene to produce a thione having the function

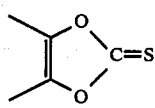

(B) ammonolyzing said thione by reacting with an agent selected from the class consisting of ammonia and lower alkyl amines to form a hydroxyaryl thionocarbamate having the function

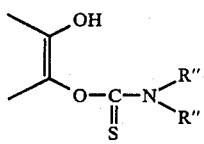

wherein R" is selected from the class consisting of hydrogen and lower alkyl groups,
(C) acetylating said thionocarbamate to form the corresponding acetoxyaryl thionocarbamate,
(D) heating in the absence of air to about 200° to 260° C for about 20 minutes to 3 hours to rearrange said thionocarbamate to form the corresponding acetoxyaryl thiolcarbamate having the function

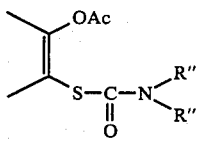

(E) distilling said acetoxyaryl thiolcarbamate to separate the corresponding oxathiol-2-one having the function

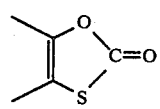

and
(F) hydrolyzing said compound to the corresponding mercaptophenol having the function

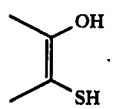

7. A method according to claim 6 further characterized in that thiophosgene is reacted with said compound containing the catechol function in basic solution slowly over from about 40 minutes to 2 hours at a low temperature between about 5° to 10° C.

8. A method according to claim 6 further characterized in that said aromatic compound containing the catechol function is selected from the class consisting of catechol, 2,3-naphthalenediol, 9,10-phenanthrenediol and corresponding substituted diols.

9. A method according to claim 6 further characterized in that said ammonolyzing agent is selected from the class consisting of ammonia, dimethylamine, diethylamine, methylethylamine, N-propylamine and N-butylamine.

10. A method according to claim 6 further characterized in that said hydroxyaryl thionocarbamate is acetylated by reaction with an acetylating agent selected from the class consisting of acetic anhydride and acetylchloride.

11. A method of preparing catechol derivatives containing the function:

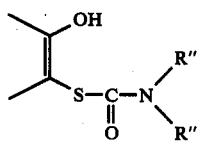

wherein R″ is selected from the class consisting of hydrogen and lower alkyl groups, which method comprises:

(A) reacting an aromatic compound containing the catechol function

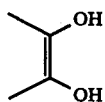

with thiophosgene to produce a thione having the function

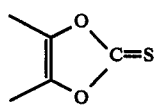

(B) ammonolyzing said thione by reacting with an agent selected from the class consisting of ammonia and lower alkyl amines to form a hydroxyaryl thionocarbamate having the function

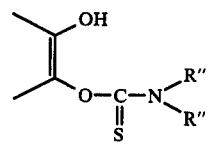

wherein R″ is selected from the class consisting of hydrogen and lower alkyl groups, (C) acetylating said thionocarbamate to form the corresponding acetoxyaryl thionocarbamate, (D) heating in the absence of air to about 200° to 260° C for about 20 minutes to 3 hours to rearrange said thionocarbamate to form the corresponding acetoxyaryl thiolcarbamate having the function

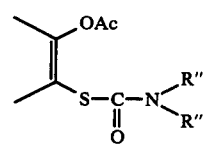

(E) distilling said acetoxyaryl thiolcarbamate to separate the corresponding oxathiol-2-one having the function

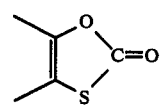

and (F) reacting said compound with an agent selected from the class consisting of ammonia and amines to form the corresponding hydroxyaryl thiolcarbamate having the function

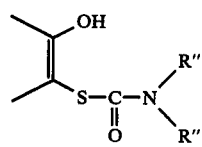

wherein R″ is selected from the class consisting of hydrogen and lower alkyl groups.

12. A method according to claim 11 further characterized in that thiophosgene is reacted with said compound containing the catechol function in basic solution slowly over from about 40 minutes to 2 hours at a low temperature between about 5° to 10° C.

13. A method according to claim 11 further characterized in that said aromatic compound containing the catechol function is selected from the class consisting of catechol, 2,3-naphthalenediol, 9,10-phenanthrenediol and corresponding substituted diols.

14. A method according to claim 11 further characterized in that said ammonolyzing agent is selected from the class consisting of ammonia, dimethylamine, diethylamine, methylethylamine, N-propylamine and N-butylamine.

15. A method according to claim 11 further characterized in that said hydroxyaryl thionocarbamate is acetylated by reaction with an acetylating agent selected from the class consisting of acetic anhydride and acetylchloride.

* * * * *